(12) United States Patent
Mastrorio et al.

(10) Patent No.: US 7,776,091 B2
(45) Date of Patent: Aug. 17, 2010

(54) ADJUSTABLE POSTERIOR SPINAL COLUMN POSITIONER

(75) Inventors: Brooke Mastrorio, Lakeville, MA (US); Shinikequa Gibson, Dorchester, MA (US)

(73) Assignee: Depuy Spine, Inc., Raynham, MA (US)

( * ) Notice: Subject to any disclaimer, the term of this patent is extended or adjusted under 35 U.S.C. 154(b) by 535 days.

(21) Appl. No.: 10/881,548

(22) Filed: Jun. 30, 2004

(65) Prior Publication Data

US 2006/0004447 A1 Jan. 5, 2006

(51) Int. Cl.
*A61F 2/44* (2006.01)
(52) U.S. Cl. .................................. 623/17.15
(58) Field of Classification Search ........ 623/17.11–16; 606/61, 72–73, 246–249, 282
See application file for complete search history.

(56) References Cited

U.S. PATENT DOCUMENTS

| 1,655,922 | A | * | 1/1928 | Stoye ........................... 606/79 |
| 2,100,319 | A | * | 11/1937 | Brown et al. ................. 433/122 |
| 5,645,599 | A | | 7/1997 | Samani |
| 6,068,630 | A | | 5/2000 | Zucherman |
| 6,126,660 | A | * | 10/2000 | Dietz ........................... 606/61 |
| 6,454,806 | B1 | * | 9/2002 | Cohen et al. .............. 623/17.15 |
| 6,730,123 | B1 | * | 5/2004 | Klopotek ................... 623/6.22 |
| 6,953,477 | B2 | * | 10/2005 | Berry ....................... 623/17.11 |
| 2002/0128716 | A1 | * | 9/2002 | Cohen et al. .............. 623/17.15 |
| 2005/0049590 | A1 | * | 3/2005 | Alleyne et al. ................. 606/61 |
| 2005/0234555 | A1 | * | 10/2005 | Sutton et al. .............. 623/17.15 |
| 2005/0256576 | A1 | * | 11/2005 | Moskowitz et al. ....... 623/17.12 |

* cited by examiner

*Primary Examiner*—Thomas C Barrett
*Assistant Examiner*—Michael J Araj

(57) ABSTRACT

Height-adjustable devices suitable for insertion between posterior spinal processes that allow the surgeon to post-operatively adjust the height of the implant.

5 Claims, 9 Drawing Sheets

FIG. 6A
FIG. 6B
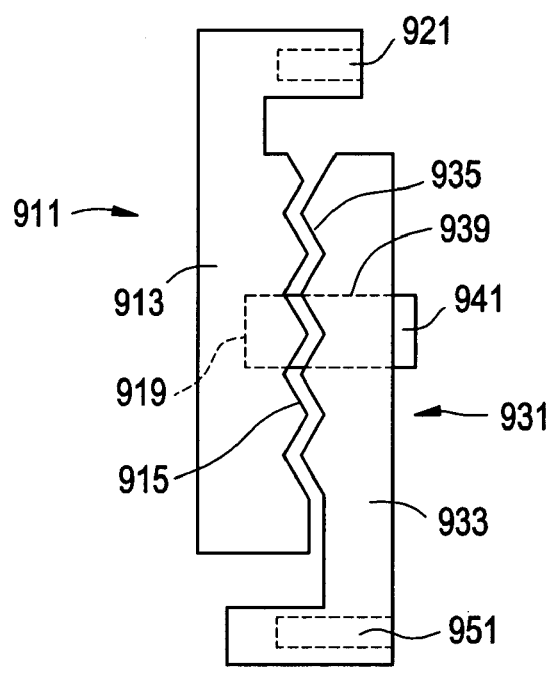
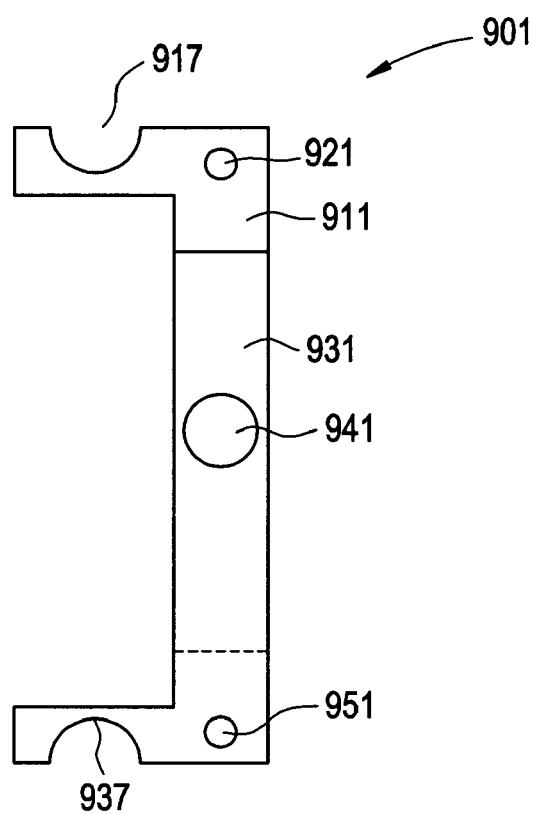

ADJUSTABLE POSTERIOR SPINAL COLUMN POSITIONER

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosis or folding of the ligamentum flavum may further compress and extend into the spinal canal. This condition, called "spinal stenosis", narrows the spinal canal and causes impingement of tissue upon the spinal cord and nearby nerves, thereby producing pain.

The "80/20" rule of spine biomechanics postulates that the posterior column of the spine supports about 20% of axial spinal forces. The muscles and ligaments in the posterior column experience tensile forces in normal spine anatomy. However, in some cases of disc replacement, the axial loads borne by the anterior and posterior columns become unbalanced. By developing an implant that re-introduces those natural tensile forces, the 80/20 balance is re-established.

There have been numerous attempts to provide relief for these afflictions by providing a spacer that inserts between adjacent spinous processes present in the posterior portion of the spinal column. This spacer essentially lifts the upper spinous process off of the lower spinous process, thereby relieving stenosis. In general, these interspinous implants are adapted to allow flexion movement in the patient, but resist or limit extension.

U.S. Pat. No. 6,068,630 ("Zuchermann") discloses a spinal distraction implant that alleviates pain associated with spinal stenosis by expanding the volume in the spinal canal or neural foramen. Zuchermann discloses a plurality of implants having a body portion and lateral wings. The body portion is adapted to seat between the adjacent spinous processes, while the wings are adapted to prevent lateral movement of the body portion, thereby holding it in place between the adjacent spinous processes.

U.S. Pat. No. 5,645,599 ("Samani") attempts to relieve spinal stenosis by essentially inserting a flexible horseshoe-shaped device between the adjacent spinous processes. Although the Samani device desirably provides a self-limiting flexibility, it nonetheless suffers from some inadequacies. For example, the Samani device does not provide for post-operative adjustment.

In sum, conventional interspinous spacers lack post-operative adjustability.

SUMMARY OF THE INVENTION

The present inventors have developed a number of height-adjustable devices suitable for insertion between posterior processes. These devices will give the surgeon the ability to alter the height between adjacent spinous processes by a segmental approach that is minimally invasive.

In a first embodiment, the device comprises a pair of hooks connected to a rod, wherein the hooks are adapted to be translatable along the rod.

In a second embodiment, the devices comprises two parallel plates and a telescoping cylinder-annulus feature therebetween that is movable axially and in the opposite direction from one another.

In a third embodiment, the device comprises a driving mechanism such as an internal gear system that axially separates the upper and lower halves of the implant.

In a fourth embodiment, the device comprises upper and lower insertion holes adapted for receipt of adjustment rods that axially separate the upper and lower halves of the implant.

In a fifth embodiment, the device comprises a threaded projection and a corresponding threaded recess that axially separate the upper and lower halves of the implant. Preferably, one of these components is magnetic, thereby allowing for non-invasive adjustment.

In a sixth embodiment, the device comprises two parallel plates and a bellows therebetween that is axially expandable.

Therefore, in accordance with the present invention, there is provided spinal implant for insertion into a space between adjacent posterior processes, the implant comprising:
    a) an upper body having:
        i. an upper bearing surface for bearing against a first posterior process, and
    b) a lower body having:
        i. an lower bearing surface for bearing against a second posterior process, the upper and lower bearing surfaces defining a height of the implant, and
    c) means for adjusting the height of the implant.

For many patients, adjusting the height of the implant would be beneficial because it would alow the surgeon to monitor pain of the patient and adjust the space between adjacent spinous processes, transverse processes or facet joints to relieve pain, or accommodate for growth or changes in the pathologies to be treated.

In some embodiments, the adjustable device of the present invention can also having an angular adjustment component, thereby allowing the surgeon to correct scoliosis, or extreme lordotic or kyphotic curves, by a segmental approach, thereby avoiding a fusion of the anterior column.

DESCRIPTION OF THE FIGURES

FIG. 1b discloses a posterior view of the complete implant of FIG. 1a.

FIGS. 6a and 6b disclose side and posteior views of an embodiment of the present invention using hooks and slidable bodies.

FIG. 7b discloses a bottom view of FIG. 7a.

DETAILED DESCRIPTION OF THE INVENTION

Figure 1A:
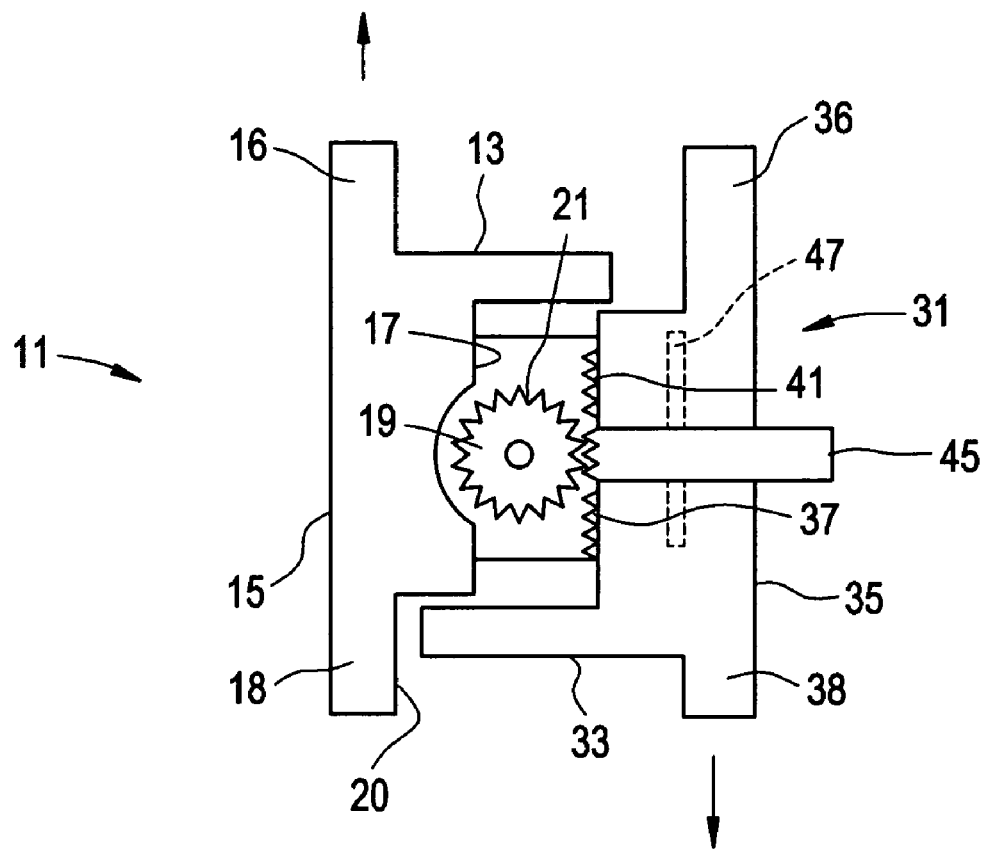
FIG. 1a discloses a cut-out view of an interspinous implant whose upper and lower bearing surfaces are separable by actuation of a gear mechanism.
Figure 1B:
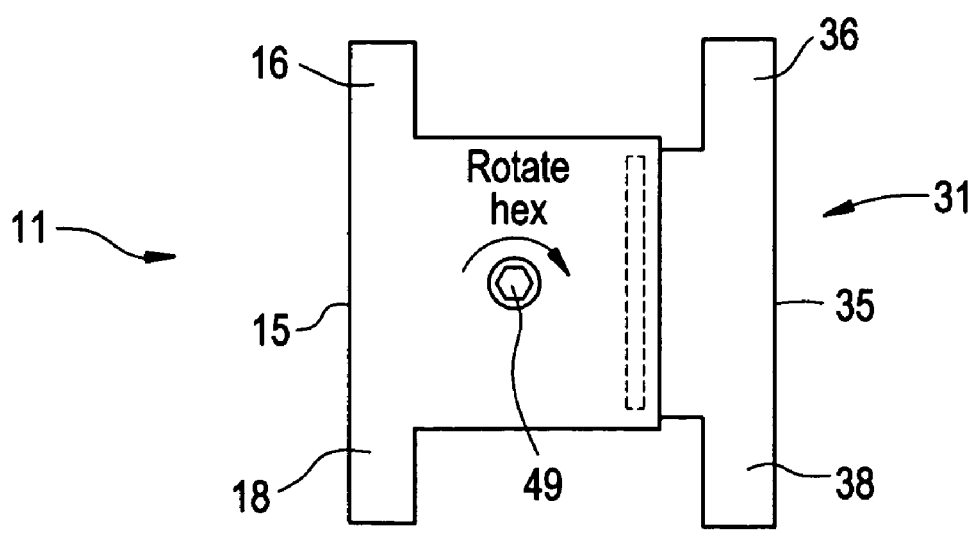

Referring now to FIGS. 1a and 1b, there is provided an interspinous implant 1 for insertion into an interspinous space between a first and second spinous process, the implant comprising:
- a) a first body 11 having:
  - i. an upper bearing surface 13 for bearing against a first spinous process,
  - ii. an outer side surface 15 having upper 16 and lower 18 extensions extending therefrom in the axial direction,
  - iii. an inner surface 17,
  - iv. a gear 19 attached to the inner surface and having a first set of teeth 21,
- b) a second body 31 having:
  - i. a lower bearing surface 33 for bearing against a second spinous process,
  - ii. an outer side surface 35 having upper 36 and lower 38 extensions extending therefrom in the axial direction, and
  - iii. an inner surface 37 having a second set of teeth 41 wherein the upper surface and the lower bearing surfaces define a height of the implant, and wherein the sets of teeth cooperate such that, upon rotation of the gear, the upper bearing surface moves relative to the second bearing surface, thereby changing the height of the implant.

As shown in FIG. 1a, the first set of teeth on the gear is radial and the second set of teeth on the second body is linear.

Because adjustability is desirable only at selected times, it is desirable that the implants of the present invention further contain a means for rendering the height non-adjustable. In preferred embodiments, a locking mechanism (such as a set screw) is positioned to contact the set of teeth on the gear and may be used to essentially stop the ratcheting nature of the rack-and-pinion components.

In one embodiment, the implant further comprises a set screw 45 and the second body has a threaded hole for accommodating a set screw, wherein the threaded hole runs from the outer surface of the second body hook to the gear teeth. Accordingly, the set screw can be percutaneously manipulated in order to allow or prevent height adjustability.

A set screw can also be used to close the gap between the two extending bodies, thereby stopping the rotation of the gear.

In some embodiments, as in FIG. 1, the one of the bodies has an axial alignment flange 47 and the other body has an alignment rail. The alignment flange nests in the rail and these features cooperate to insure that rotational movement of the gear is translated into purely linear relative movement of the bodies. In other embodiments, a pin-and-slot mechanism may be used to accomplish the same goal.

In some embodiments, an actuation rod (not shown) is attached to the center of the gear and extends to the surface of the implant. Therefore, the gear can be actuated by rotating the actuation rod. This allows for percutaneous actuation of the height-adjustable implant. In preferred embodiments, the proximal end portion of the rod has a hexagonal port 49.

In some embodiments, the gear can be magnetic, and thus susceptible to rotation when under the influence of a magnetic field. In such embodiments, there is no need for a driver access port on the implant for actuating the gear.

In preferred embodiment, the bearing surface 33 of one of the bodies extends substantially entirely to the inner side 20 of the opposing extension 18 of the other body. When the bear surface extends so far, the implants maximizes the surface area with which it can support the adjacent processes, thereby minimizing stress upon the implant.

In another embodiment of the present invention using gears to produce translation of opposed surfaces and effect height adjustment, and referring now to FIGS. 2a-2d, there is provided an interspinous implant 801 for insertion into an interspinous space between a first and second spinous process, the implant comprising:
- a) a first body 811 having:
  - i. an upper bearing surface 813 for bearing against a first spinous process,
  - ii. an outer side surface 815 having upper 816 and lower 818 extensions extending therefrom in the axial direction,
  - iii. an inner surface 817,
  - iv. a gear 819 attached to the inner surface and having a first set of teeth 821,
- b) a second body 831 having:
  - i. a lower bearing surface 833 for bearing against a second spinous process,
  - ii. an outer side surface 835 having upper 836 and lower 838 extensions extending therefrom in the axial direction, and
  - iii. an inner surface 837 having a second set of teeth 841 wherein the upper surface and the lower bearing surfaces define a height of the implant, and wherein the sets of teeth cooperate such that, upon rotation of the gear, the upper bearing surface moves relative to the second bearing surface, thereby changing the height of the implant.

Figure 2A:
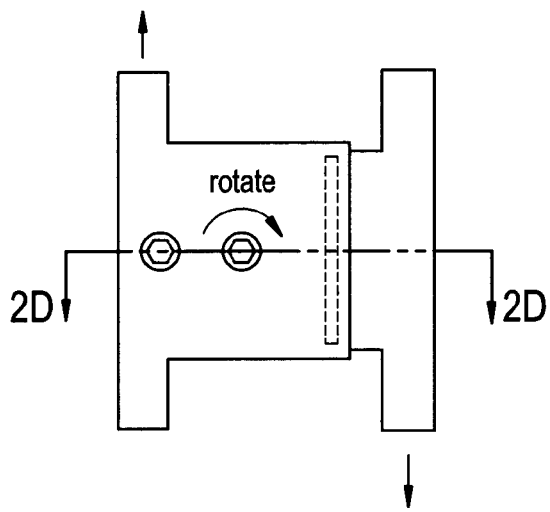
FIGS. 2a-2d disclose posterior, posterior cross-sectional, exploded isometric and top axial cross-sectional views of a device of the present invention.
Figure 2B:
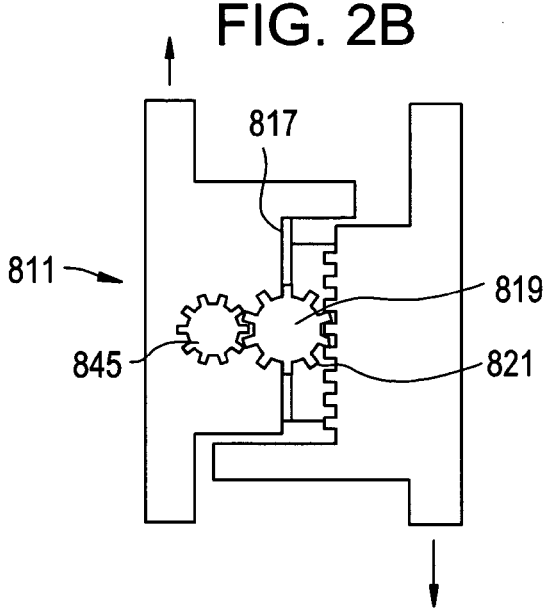
Figure 2C:
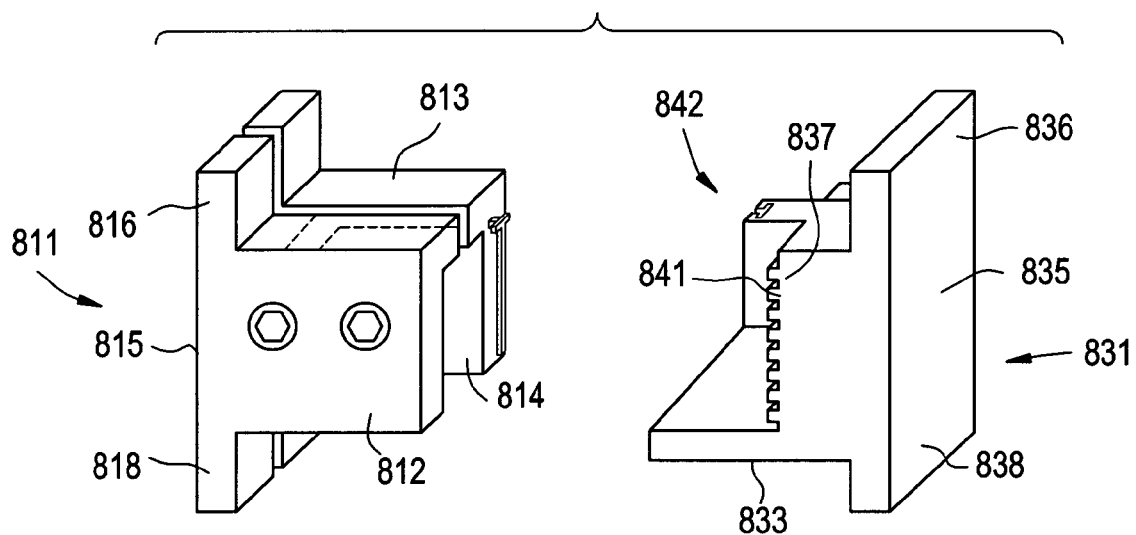
Figure 2D:
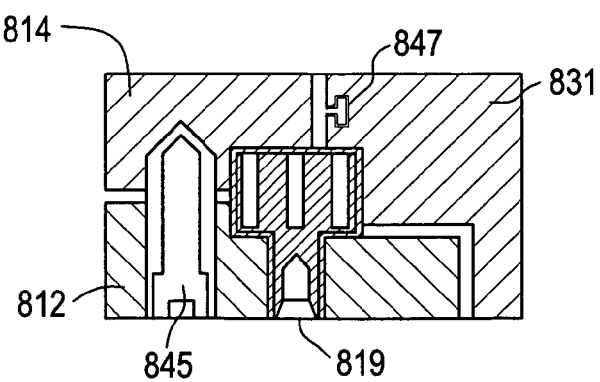
Figure 3:
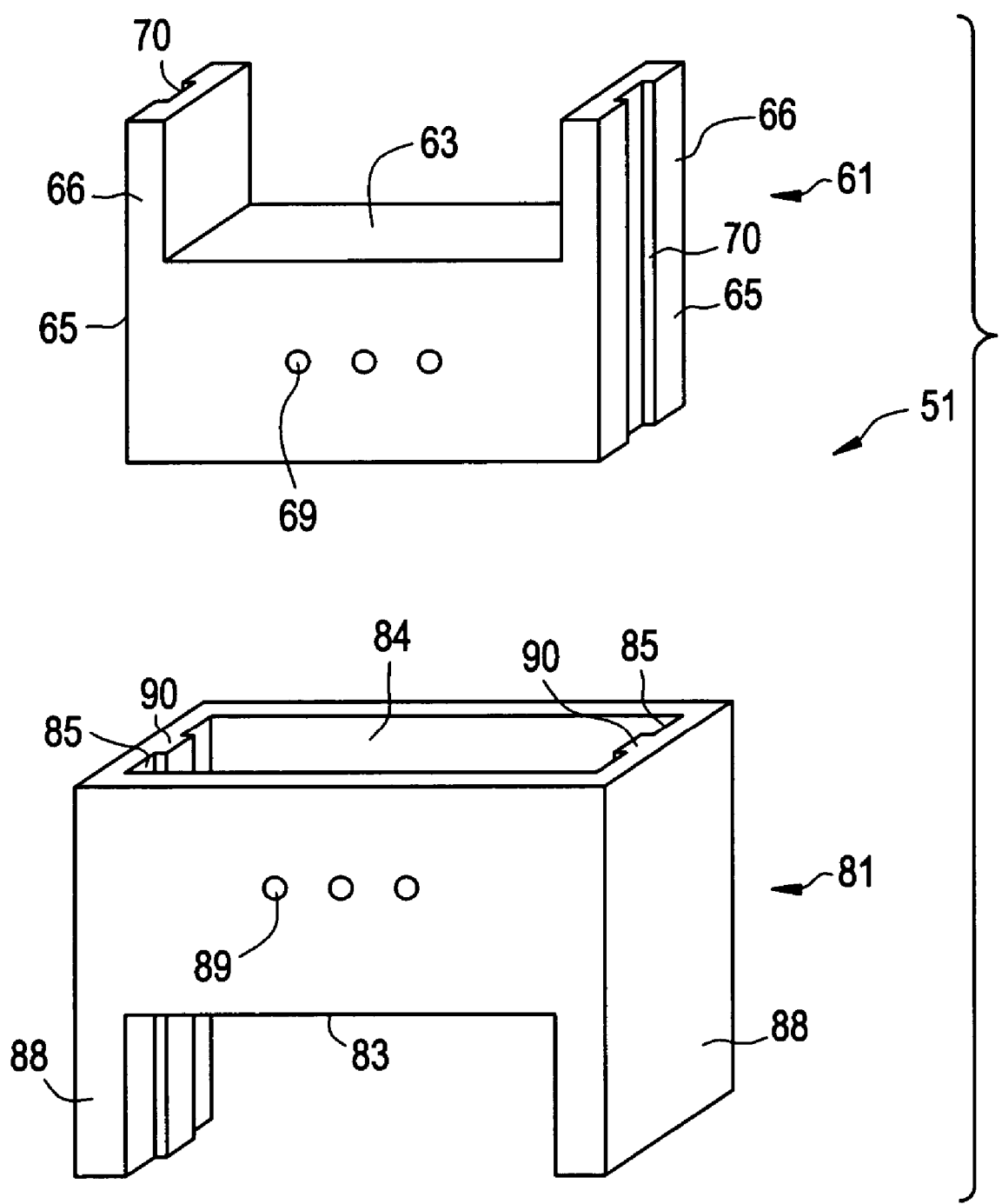
FIG. 3 discloses an exploded isometric view of another embodiment of the present invention.

In some embodiments, as best seen in FIG. 2c, first body 811 may optionally include two half-bodies 812 and 814. When provided in this configuration, a set screw 845 may be inserted across each half-body (as shown in FIG. 2d) and used to close or open the half-bodies. In their open position, the half-bodies do not interfere with the rotation of gear 819. In their closed position, however, the half-bodies prevent rotation of the gear.

In some embodiments (as in FIG. 2d), the first and second bodies are adapted to possess a T-slot guiding mechanism 847, comprising a T-slot and a corresponding T-projection. These features are provided to control the extension of the first and second bodies. In some cases using the T-slot and T-projection, extension of the two bodies can be controlled by the gear (as shown), while in others, extension can be controlled by a distraction device.

In other embodiments, a dovetail feature may be provided on the first and second bodies for guiding the extension.

Figure 9:
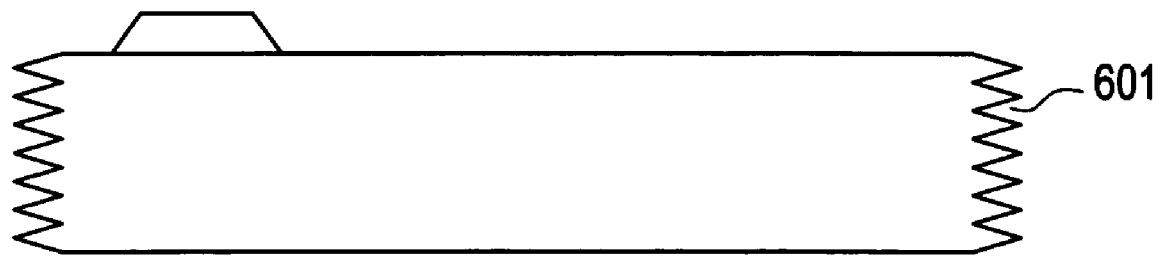
FIG. 9 discloses an interspinous implant whose upper and lower bearing surfaces are separable by inflation of a bellows.
Figure 10:
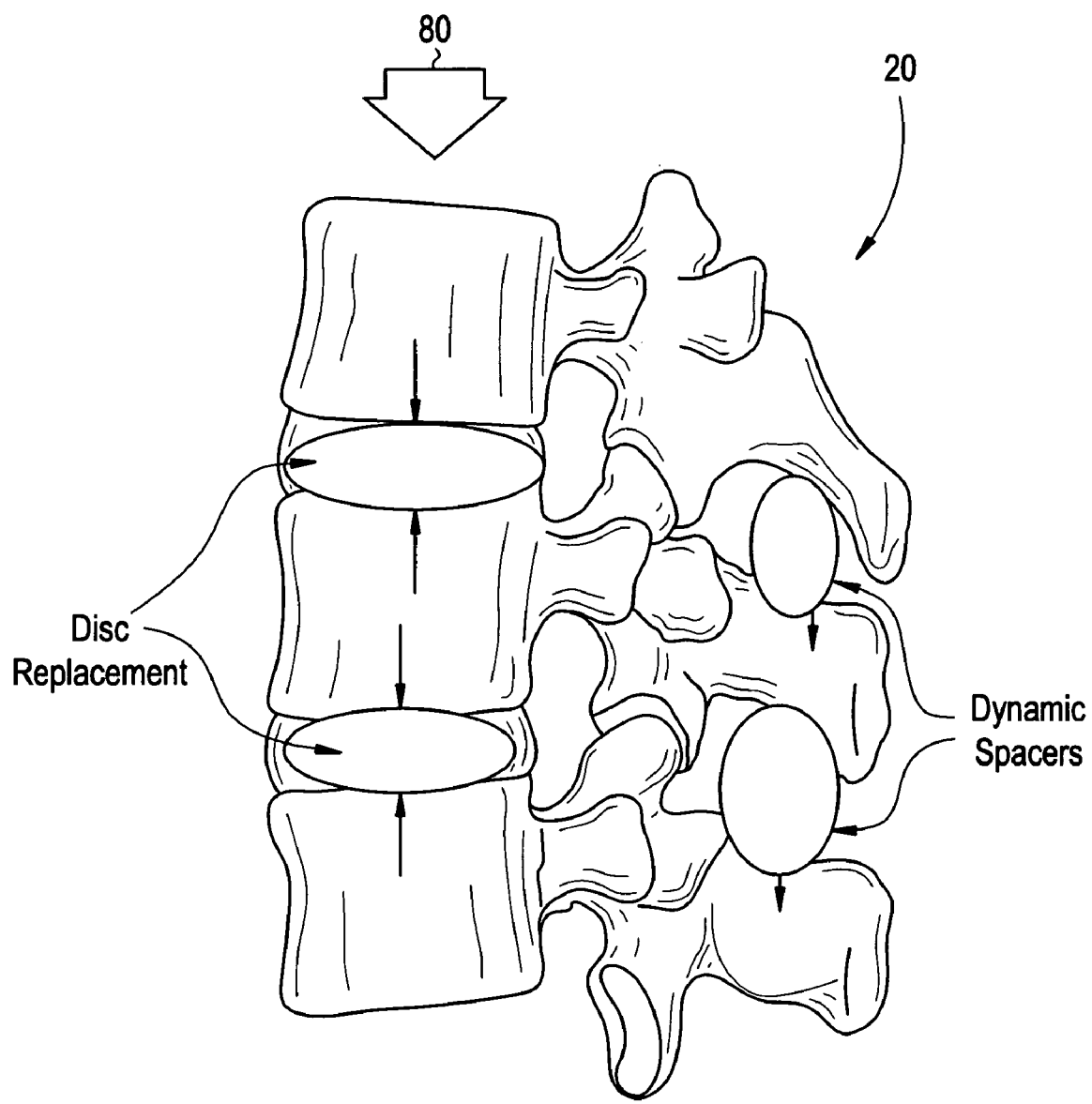
FIG. 10 is a prior art diagram of a natural functional spinal unit.

In another embodiment of the present invention using a distraction device and translation of opposed surfaces to effect height adjustment, and referring now to FIG. 9, there is provided an interspinous implant 51 for insertion into an interspinous space between a first and second spinous process, the implant comprising:
- a) a first body 61 having:
  - i. an upper bearing surface 63 for bearing against a first spinous process,
  - ii. outer side surfaces 65,
  - iii. upper extensions 66 extending from the outer side surfaces in the axial direction, iv. a longitudinal recess 70 extending into each outer side surface and upper extension in the transverse direction, and iv. a first plurality of holes 69 adapted for attachment to an insertion instrument, b) a second body 81 having:

i. a lower bearing surface 83 for bearing against a second spinous process, ii. a recess 84 defining inner side surfaces 85, iii. lower extensions 88 extending from each inner side surface in the axial direction, iv. longitudinal projections 90 extending from each inner side surface and lower extension in the transverse direction, v. a second plurality of holes 89 adapted for attachment to an insertion instrument, wherein the upper surface and the lower bearing surfaces define a height of the implant, and wherein the longitudinal projection is adapted for slidable reception within the longitudinal recess, so that the upper bearing surface may move relative to the second bearing surface, thereby changing the height of the implant.

In this embodiment, the slidable reception of the longitudinal projection within the longitudinal recess allows the upper bearing surface to move relative to the second bearing surface, thereby changing the height of the implant.

In use, insertion instruments are inserted into the holes sets and either a) moved toward one another to decrease the height of the device or b) moved away from one another to increase the height of the device. A set screw (not shown) is preferably used to lock and unlock the longitudinal projection/recess assembly.

Figure 4:
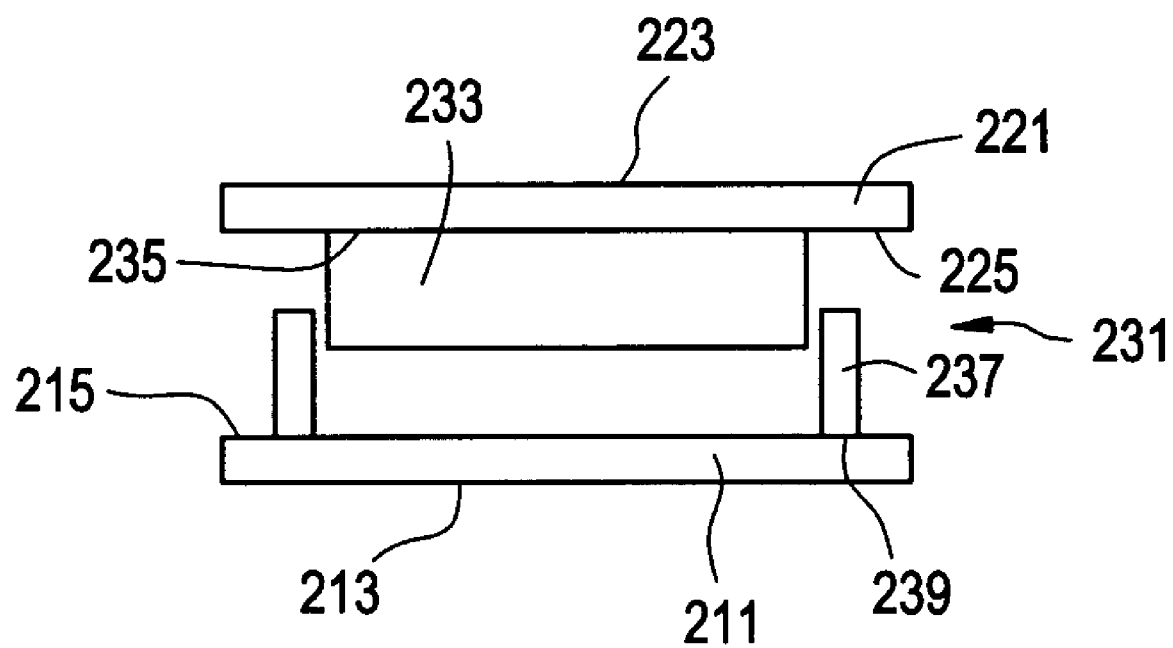
FIG. 4 discloses an interspinous implant whose upper and lower bearing surfaces are separable by a telescoping mechanism.

Now referring to FIG. 4, there is provided an interspinous implant 201 for insertion into an interspinous space between an upper and lower spinous process, the implant comprising:

a) a lower base 211 having a lower bearing surface 213 adapted for fixation to an upper side of the lower spinous process and an upper surface 215, b) an upper base 221 having an upper bearing surface 223 adapted for fixation to a lower side of the upper spinous process and a lower surface 225, and c) a height-adjustable container 231 having a lower portion attached to the lower base and an upper portion attached to the upper base.

In this particular embodiment, the height-adjustable container comprises:

i) an upper projection (here, a cylinder) 233 having an upper surface 235 attached to the lower surface of the upper base and an outer radius, and ii) a lower recess (here an annulus) 237 having a lower surface 239 attached to the upper surface of the lower base, and having an inner radius, wherein the outer and inner radii are adapted to provide a telescoping action in the height adjustable container.

In some embodiments, as in FIG. 9, the telecopic action means may be replaced by a bellows 601. Preferably, the bellows comprises a port adapted for the introduction of a fluid.

As above, this implant may also further contain a means for rendering the height non-adjustable. In preferred embodiments, a set screw may be used to contact each of the annulus and cylinder components to essentially stop the telescoping action.

In some embodiments, the height of the container may be adjusted by altering an amount of fluid disposed within the container cavity. The fluid may be a liquid, gas or gel.

Figure 5A:
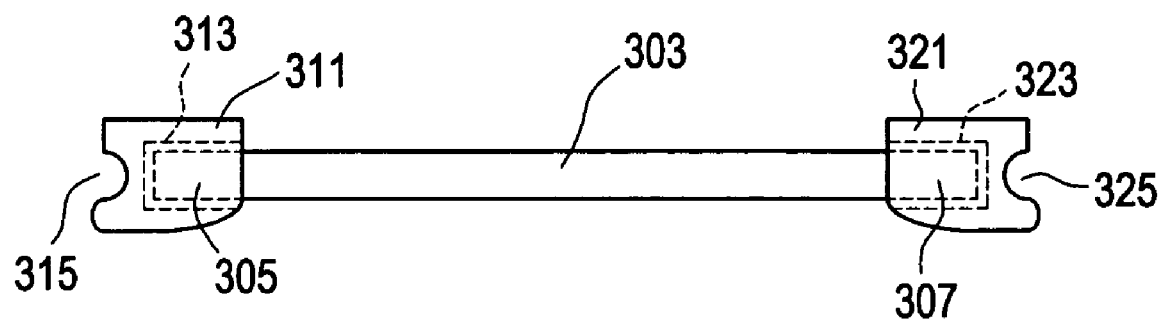
FIG. 5 discloses an interspinous implant whose upper and lower bearing surfaces are separable by translatable hooks.

Referring now to FIG. 5*a*, there is provided an interspinous implant 301 for insertion into an interspinous space between adjacent posterior processes, comprising:

a) a central longitudinal body 303 having a diameter and first 305 and second 307 ends defining a length at least as great as the distance between adjacent posterior processes, b) a first hook 311 having a bore 313 adapted for slidable connection to the central longitudinal body and a concave bearing portion 315 adapted for bearing against a first posterior process, and c) a second hook 321 having a bore 323 adapted for slidable connection to the central longitudinal body and a concave bearing portion 325 adapted for bearing against a second posterior process, wherein the first end of the central longitudinal body is received within the first bore, and the second end of the central longitudinal body is received within the second bore.

Because the concave bearing portions of the hooks of FIG. 5*a* open in opposite directions, the implant is desirably used to maintain the height of a space, such as the interspinous space between adjacent spinous processes.

In this embodiment, each hook is shown as being slidable along the rod. Having two translatable hooks allows for twice as much of a maximum adjustability length; provides for more adjustment options when working around bony anatomy, and provides both increased flexibility and stability. However, in other embodiments, one of the hooks may be fixed to the central longitudinal body. Requiring that only a single hook be slidable reduces the time required to make the desired height adjustment.

In this embodiment, the concave bearing portion of each hook is shown as being essentially in-line with the rod. This is advantageous because the rod will be under compressive stresses. However, in other embodiments (not shown), the concave bearing portion of each hook may be offset from the rod axis. The offset nature of the hooks is advantageous because it allows the hooks to possess a greater range of travel along the rod.

Because adjustability is desirable only at selected times, it is desirable that the implants of the present invention further contain a means for rendering the height non-adjustable. In preferred embodiments, a locking mechanism, such as set screw 331, is positioned in a threaded bore within a hook, is adapted to contact the rod and may be used to essentially stop the slidable nature of the hooks.

In one embodiment, the implant comprises a set screw and each slidable hook has a threaded hole for accommodating a set screw, wherein the threaded hole runs from the outer surface of the hook to the rod. Accordingly, the set screw can be percutaneously manipulated in order to allow or prevent height adjustability.

In some embodiments, each hook can include a hole on its posterior surface adapted for insetion of a tyne of a forceps instrument. When the tynes are inserted into these holes, manipulation of the separation distances between the tynes adjusts the height of the implant.

Figure 5B:
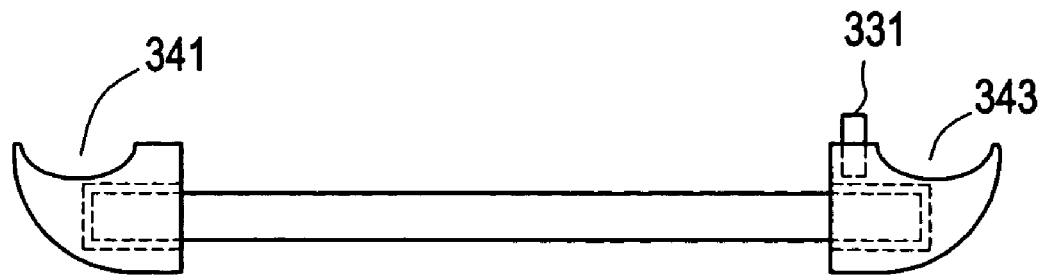

In some embodiments, the rod or gear can be magnetic, and thus susceptible to rotation when under the influence of a magnetic field. In such embodiments, the rod preferably includes a first thread that threadably mates with the threaded bore of first hook and a second reverse thread that threadably mates with the threaded bore of the second hook Now referring to FIG. 5b, there is provided a height adjustable posterior implant that is substantially the same as that of FIG. 1a, except that the concave bearing portions 341, 343 open in the same direction, substantially transverse to the longitudinal axis of the rod. This implant is desirably fitted to adjacent transverse proceses in order to compress the distance therebetween. Accordingly, it is believed that this implant would have an advantageous use in correcting scoliosis, or in adjusting the angle of the anterior disc space to a more lordotic or kyphotic orientation.

Referring now to FIG. 6, there is provided an interspinous implant 301 for insertion into an interspinous space between adjacent posterior processes, comprising:
a) an upper body 911 having an upper bearing surface 917 adapted for bearing against an upper posterior process and a longitudinal shank 913 having a first plurality of teeth 915, a locking hole 919 and a distraction hole 921, and
b) a lower body 931 having a lower bearing surface 937 adapted for bearing against a lower posterior process and a longitudinal shank 933 having a second plurality of teeth 935, a locking hole 939 and a distraction hole 951, and
c) a set screw 941 disposed within both of the locking holes, wherein the first plurality of teeth engage the second plurality of teeth.

The devices of the present invention may include conventional actuation means well known to the person of the ordinary skill in the art to adjust the height of the device.

In some embodiments, mechanical actuators are used. In one preferred example, a percutaneous approach is used to deliver the distal end of a driver (e.g., screwdriver or hexdriver) to a port in the device. Upon rotation of the driver, the height of the implant is adjusted. See FIGS. 1, 4 and 5.

Figure 7A:
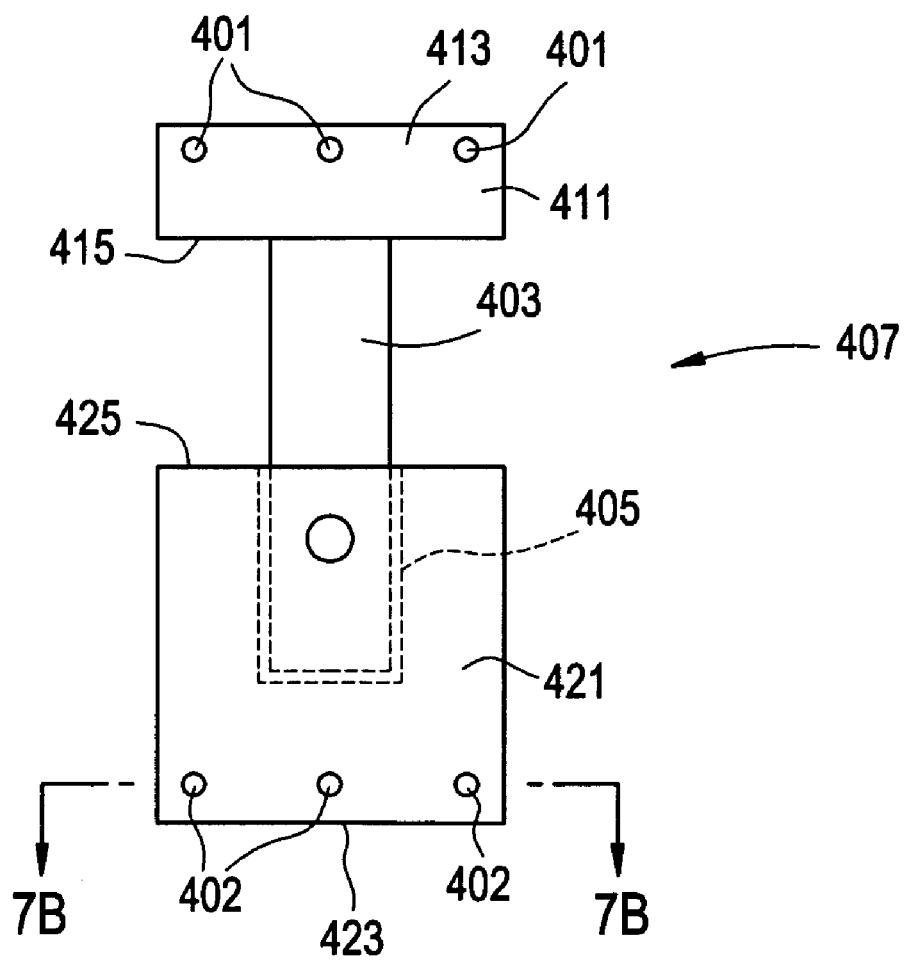
FIG. 7a discloses an interspinous implant whose upper and lower bearing surfaces are separable by the insertion and spreading of distraction rods.

Now referring to FIG. 7a, there is provided an interspinous implant for insertion into an interspinous space between an upper and lower spinous process, the implant comprising:

a) a first base 411 having an outer bearing surface 413 adapted for fixation to an end of the first spinous process, an inner surface 415 and a first extension 403 extending from the inner surface, b) an second base 421 having an outer bearing surface 423 adapted for fixation to an end of the second, an inner surface 425, and a recess 405 in the inner surface, wherein the extension is adapted for slidable reception within the recess In some embodiments, the device comprises a plurality of holes located substantially on the same face of the implant and on upper and lower portions of the implant. In the case of FIG. 7a, three holes 401 are provided on the upper portion of the implant, and three holes 402 are provided on the lower portion of the implant. When compression or distraction rods (not shown) having diameters corresponding to their associated holes are inserted into the holes, the height of the device may be adjusted by increasing or reducing the distance between the rods. In the case of FIG. 4a, the height of the implant is adjusted by the telescoping action produced by cylinder 403 and annulus 405.

Figure 7B:
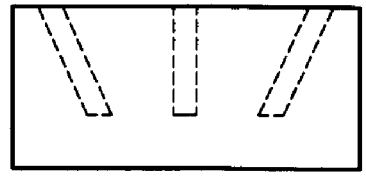

Now referring to FIG. 7b, in preferred embodiments, the holes extend at least one-quarter of the depth of the implant, more preferably at least one-half the depth of the implant. This feature minimizes any cantilever effect.

In some embodiments, the extension has an outer surface that is smooth. In others the extension has an outer surface that is threaded.

In some embodiments, the implant further comprises a set screw received within the second base and positioned to contact the extension.

In some embodiments, the implant has a magnetic component such that the height adjustment can driven by movement of an external magnet. These embodiments are advantageous because the height adjustment may be accomplished completely non-invasively.

In other embodiments, the device includes an internal motor capable of being powered by an external magnetic field, also allowing height adjustment to be accomplished completely non-invasively.

Figure 8:
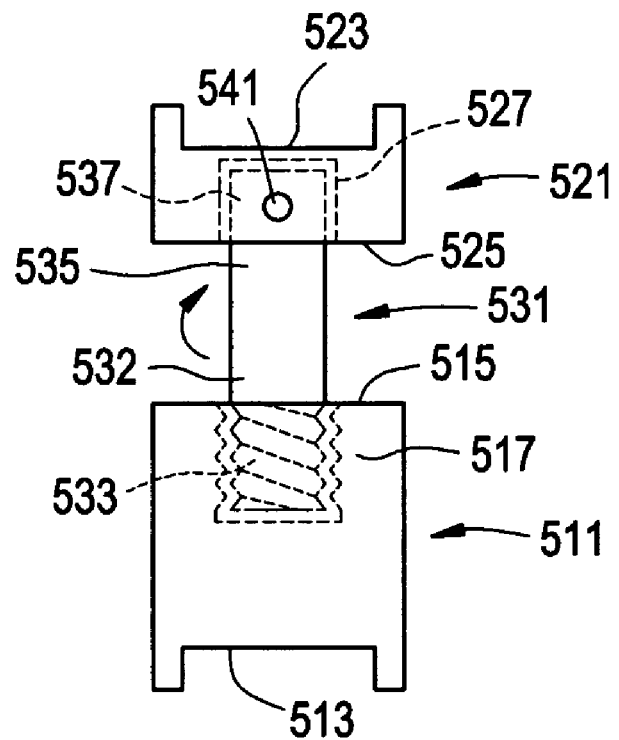
FIG. 8 discloses an interspinous implant whose upper and lower bearing surfaces are separable by a rotation of a thread.

For example, and now referring to FIG. 8, there is provided an interspinous implant 501 for insertion into an interspinous space between an upper and lower spinous process, the implant comprising:
a) a lower base 511 having a lower bearing surface 513 adapted for fixation to an upper side of the lower spinous process and an upper surface 515 having a threaded recess 517 therein,
b) an upper base 521 having an upper bearing surface 523 adapted for fixation to a lower side of the upper spinous process and a lower surface 525 having a smooth recess 527 therein, and
c) a longitudinal rod 531 having a lower portion 532 having a threaded end 533 and an upper portion 535 having a smooth end portion 537, wherein the threaded end portion of the longitudinal rod is threadably received in the threaded recess of the lower base, and wherein the smooth end portion of the longitudinal rod is slidably received in the smooth recess of the upper base.

In preferred embodiments, the slidable action of the upper smooth recess and rod end portion may be checked by a set screw 541 positioned to contact the rod.

In some embodiments, the implant of FIG. 8 further comprises a plurality of holes in each of the upper and lower bases, wherein the holes are adapted for attachment to a compression or distraction instrument.

In some embodiments, the extension of the implant of FIG. 8 has an outer surface that is smooth. In others, it has an outer surface that is threaded.

In some embodiments, the implant further comprises a first set screw received within the first base and positioned to contact the rod. In some embodiments, the implant further comprises a second set screw received within the second base and positioned to contact the rod.

In some embodiments, the implant has an expandable container such that the height adjustment can be achieved by adding a fluid to the container, such as a liquid, gas or gel. These embodiments are advantageous because the height adjustment may be accomplished percutaneuously with a high gauge needle.

In some embodiments (now shown), the deep portion of the recess includes a recessed lip projecting outward from the periphery of the recess, and the deep end of the smooth end portion 537 of the rod 531 includes a transverse projection adapted to fit within the lip, but not within the remaining width of the recess. These features provide a stop that insures that the smooth end portion of the rod will not disengage from the recess.

The implants of the present invention may be used in many locations about the posterior portion of the human spine. In some embodiments, the device may be an interspinous device, adapted to be inserted between adjacent spinal processes. In others, the device may be adapted to be inserted between adjacent transverse processes. In others, the device may be adapted to be inserted between adjacent facets defining a facet joint.

In some embodiments, the height-adjustable devices are used in conjunction with a devices placed on the anterior side of the spines, such as a disc replacement device, a nucleus pulposus augmentation device, or a fusion device such as a mesh or a cage. The use of a height-adjustable posterior device with an anteriorly-placed device is advantageous because it provides for a minimally invasive, post-operative correction of problems such as implant subsidence, range of motion, and pain.

The device may also be used for temporal tailoring of physiologic processes. For example, in one embodiment used in conjunction with an anterior device having surfaces adapted for bony ingrowth, the posterior device is inserted in a manner so as to compress the anterior portion of the spine, thereby speeding the bony ingrowth through the anterior device. After such in-growth occurs, the height of the posterior device is adjusted so as to lessen the compression experienced on the anterior portion of the spine.

In other embodiments, the locking mechanism of the device may be loosened to allow for greater freedom of movement of the device.

In some embodiments, the height-adjustable device is implanted at the time of implantation of the disc replacement device or nucleus pulposus augmentation device. In others, the height-adjustable device is implantation at the time of revision of the disc replacement device or nucleus pulposus augmentation device.

In most of the embodiments presented above, the upper and lower bearing surfaces of the device are shown as being essentially flat. In other embodiments, however, these surfaces are shaped to provide greater correspondence with the bony anatomy against which they bear. For example, when the device is an interspinous process, the bearing surfaces may be concave in order to correspond with the convex nature of the opposing spinous processes. In other embodiments adapted for placement within a facet joint, the bearing surfaces have a large radius to correspond with the relatively large radius of the natural facets.

In most of the embodiments presented above, the adjustment results in essentially linear displacement of the upper and lower bearing surfaces of the device. In other embodiments, however, the adjustment meachanisms are adapted to provide angular displacement as well. For example, in some embodiments, the device has corresponding curved sliding surfaces, whereby their relatively movement causes a change in the relative angle of the upper and lower bearing surfaces. In some embodiments, thereof the curved sliding surfaces are fromed by a polyaxial sphere-in-cup arrangement.

Although the locking means set forth above typically present a set screw, other locking means may be employed. In some embodiments, the locking mechanism may be selected from the group consisting of a set screw, a spring-loaded ratchet-and-pawl, a spring-loaded pin-and-detent, and a wedged thread having spring-loaded balls. In some embodiments, the locking mechanism is magnetic, so that the locking and unlocking of the locking mechanism may be accomplished by an external magnet.

The devices of the present invention may be used advantageously in many situations. For example, the height of the implant may be adjusted in order to increase or decrease the spacing between spinous processes until the desired patient result is obtained. For example, it may be adjusted to shift sections of the vertebral bodies until nerve compression or other pathology is reduced, thereby minimizing pain and obviating the need for other invasive surgical procedures.

The height may be adjusted based upon pain feedback from the patient.

Multiple devices may be used in order to adjust multiple segments in the same session. This would have advantage in the management of scoliosis (as it allows for incremental adjustments over time, and of pain and nerve impingement.

The height of the device may be adjusted to accommodate growth of the patient.

The height of the device may be adjusted to reflect a change in pathology (e.g., as a degenerative disease progresses).

In cases wherein an anterior device has been implanted, the height of the posterior device may be adjusted in order to re-establish the proper 80/20 load sharing balance. As noted above, the device of the present invention may also be used to initially deliberately load a graft placed in the anterior portion of the spine, and then adjusted to release the load once sufficient bone growth has occurred.

In some embodiments, the device of the present invention may include an adjunct feature designed to further patient outcome. For example, in some embodiments, the device may include an injection port for the delivery of medications, such as narcotics. In some embodiments, the device may include electrodes for the facilitation of spinal nerve stimulation or bone growth. In some embodiments, the device may include magnets for bone growth promotion.

In some embodiments of the present invention, MEMS technology sensors and actuators may be incorporated into the device allowing the physician to make adjustments or gather data either automatically or telemetrically.

In some embodiments, a battery may be used to drive the adjustment mechanism of the device. In some embodiments thereof, the battery is located internally, either within or adjacent to the implanted device. In others, the battery is located external to the patient and is electrically connected to the device by a needle.

In some embodiments, the adjustment is actuated by a component having shape memory capabilities. Such components have the ability to superelastically change their shapes in response to a temperature change. Therefore, when a device having a shape memory component is used, the surgeon will be able to adjust the height of the device by simply changing the temperature of the shape memory component.

In some embodiments, the adjustment is actuated by a piezoelectric component. Such components have the ability to vibrate in response to electric current. Therefore, when a device having a piezoelectric component is used, the surgeon will be able to adjust the height of the device by simply vibrating a piezoelectric component adapted to act as an actuator of a threaded component.

The implants of the present invention may be suitably manufactured from any suitable biomaterial, including metals such as titanium alloys, chromium-cobalt alloys and stainless steel) and polymers (such as PEEK, carbon fiber-polymer composites and UHMWPE.

In some embodiments, the device is specifically manufactured for a specific individual. In preferred embodiments thereof, an MRI of the patient is taken, and is used as input to a computer-aided design (CAD) device to produce a device having at least one patient-specific contoured surface. The contouring of that surface may be accomplished conventional methods such as machining or casting.

Because of the dynamic nature of the device of the present invention, in some embodiments, there may be a concern that its expansion may produce a new issue. For example, there may be a concern that expansion produces a newly created void in the device that may undesirably promote tissue ingrowth. In another example, there may be a concern that expansion or height reduction causes impingement of a surface upon a nearby nerve.

Therefore, in some embodiments, the device is encapsulated in an external housing (such as silicone). The housing preferably can be stretched in the amount desired in the expansion without generating undue stress. In one preferred embodiment, the external housing covers a bellows component of the device.

I claim:

1. A spinal implant for insertion into a space between a first and second posterior process, the spinal implant comprising:
   a) a first body having:
      i. an upper bearing surface for bearing against a first process,
      ii. an outer side surface having upper and lower extensions extending therefrom in an axial direction,
      iii. an inner surface
      iv. a gear attached to the inner surface having a first set of teeth, each tooth having an apex,
   b) a second body having:
      i. a lower bearing surface for bearing against a second process,
      ii. an outer side surface having upper and lower extensions extending therefrom in the axial direction,
      iii. an inner surface having a second set of teeth, each tooth having an apex,
   wherein the first set of teeth is radial and the second set of teeth is linear,
   and wherein the apex of each tooth in the first set of teeth is in a radial arrangement relative to each other,
   and wherein the apex of each tooth in the second set of teeth is in a linear arrangement relative to each other,
   wherein the first set and second set of teeth cooperate such that, upon rotation of the gear, the upper bearing surface moves relative to the lower bearing surface, thereby changing a height of the spinal implant.

2. The implant of claim 1 further comprising a locking mechanism positioned to fix the gear.

3. The implant of claim 1 further comprising an actuation rod attached to the center of the gear.

4. The implant of claim 1 wherein the gear is magnetic.

5. The implant of claim 1 wherein at least one bearing surface extends substantially to an inner side of one of the extensions.

* * * * *